United States Patent [19] … [11] Patent Number: 4,880,751
Georghegan … [45] Date of Patent: Nov. 14, 1989

[54] IMMUNOGLOBULIN ADSORPTION
[75] Inventor: William D. Georghegan, Houston, Tex.
[73] Assignee: Board of Regents, The University of Texas System, Austin, Tex.
[21] Appl. No.: 926,080
[22] Filed: Oct. 31, 1986
[51] Int. Cl.⁴ .................. G01N 33/53; G01N 33/543; G01N 33/563; G01N 33/544
[52] U.S. Cl. ................................... 436/518; 436/512; 436/519; 436/525; 436/527; 436/529; 436/530; 436/531; 436/823; 435/7; 530/388
[58] Field of Search ............... 436/518, 519, 525, 527, 436/529, 530, 531, 512, 823; 530/387, 388, 830; 435/7; 424/3

[56] References Cited
U.S. PATENT DOCUMENTS 4,145,406  3/1979  Schick et al. ........................ 436/541
4,208,479  6/1980  Zuk et al. ............................. 435/7
4,313,734  2/1982  Leuvering ......................... 23/230 B
4,446,238  5/1984  DeMey et al. ....................... 436/527

FOREIGN PATENT DOCUMENTS 0158746 10/1985 United Kingdom .................... 435/7

OTHER PUBLICATIONS

Faulk et al. (1971), *Immunochemistry*, 8:1081.
Romano et al. (1974), *Immunochemistry*, 11:521.
Horisberger et al. (1975), *Experientia*, 31:1147.
Bauer et al. (1975), *Experientia*, 31:1149.
Horisberger et al. (1977), *Jrnl. Histochem. Cytochem.*, 25:295.
Geoghegan et al. (1978), *Immunol. Comm.*, 7:1.
Geoghegan et al. (1980), *Jrnl. Immunol. Meth.* 34:11.
Geoghegan et al. (1981), *Immunology*, 44:331.
Goodman et al. (1981), *Jrnl. Microscopy*, 123:201.
DeMey et al. (1981), *Prot. Biol. Fluids, pp. 173-176.*
DeMey et al. (1981), *Cell Biol. Intl. Rep.*, 5:889.
Warchol et al. (1982), *Histochemistry*, 76:567.
DeWaele et al. (1983) in *Techniques in Immunocytochemistry*, Vol. 2, pp. 1-22.
DeMey (1983) in *Immunochemistry: Practical Applications in Pathology and Biology*, pp. 82-112, Eds. J. Polak and S. Van Noorden.
DeMey (1983), in *Immunochemistry*, pp. 347-369, Ed. A. C. Cuello.
Handley et al. (1983), *Proceedings Society Exp. Biol. and Med.*, 174:1-2.
Tinglu et al. (1984) *Jrnl. Bacteriol.*, 159:668.
Slot et al. (1984) in *Immunolabelling for Electron Microscopy*, pp. 129-141.
Colloidal Metal Marking Reference Book (1984), pp. 1-7.
Wang et al. (1985), *Histochemistry*, 83:109.
Geoghegan (1985), *Jrn. Cell Biol.* 101:85A, presented at 25th Annual ASCB Meeting, Nov. 18-22, 1985.
Poster presented at 25th Annual ASCB Meeting, Nov. 18-22, 1985.
Park et al. (1986), Jrnl. Colloid Interface Sci., 111:197.
Dialog Search Report.
Geoghegan et al. (1977), *Jrnl. Hist. Cytochem.*, 25:1187.
Bagchi and Birnbaum, *J. Colloid and Interface Science*, 83:460-478 (1981).
Morrissey and Hand, *J. Colloid and Interface Science*, 65:423-431 (1978).
Handley and Chien, *Proceedings of the Society for Experimental Biology and Medicine*, 174:1-11 (1983).

Primary Examiner—Sam Rosen
Assistant Examiner—Florina B. Hoffer
Attorney, Agent, or Firm—Arnold, White & Durkee

[57] ABSTRACT

The present disclosure is directed to methods for the preparation of immunoadsorption matrices having IgG molecules adsorbed thereto in a preferred configuration, i.e., adsorbed to the matrix by their (Fc) rather than F(ab) portions. IgG molecules, are selected such that the F(ab) portion of the IgG fraction adsorbed has a more acidic or basic net isoelectric point or pI range than the F(c) end of the molecule, depending on the characteristics of the adsorption surface. For negatively charged surfaces, IgG molecules having relatively alkaline F(c) portions are selected. For positively charged surfaces, IgG with relatively acidic F(c) portions are selected. Additional selection criteria include pI fractionation to provide fractions having well defined pI characteristics as defined by "non-overlap" or "pI range" of F(c) and F(ab) portions pI's. Methods disclosed are particularly well suited to the preparation of colloidal gold immunostains.

25 Claims, 4 Drawing Sheets

IMMUNOGLOBULIN ADSORPTION

BACKGROUND OF THE INVENTION

The government may own certain rights in the present invention pursuant to NIH Grant 5-R23-AM35362-01.

1. Field of the Invention

The present invention relates to improved methods applicable to the adsorption of immunoglobulin molecules to selected surfaces. In particular, the invention is directed to the selection and fractionation of IgG species, and to processes for achieving preferential adsorption of the F(c) portion of the IgG molecules to selected surfaces relative to their F(ab) portions.

2. Description of the Related Art

The ability of immunoglobulin molecules, and in particular IgG molecules, to form specific antibody/antigen complexes in vitro, had led to their widespread use in a number of clinical diagnostic settings. For example, specific antibodies, both monoclonal and polyclonal, are useful tools in the diagnosis of numerous disease states where the identification and/or quantification of specific antigens in a particular sample is indicative of a disease state. Such immunological tools take many possible forms, ranging from absorption immunochromatography for the isolation of specific antigens, to techniques for immunodectection, such as radioimmunoassay (RIA) and enzyme-linnked immunosorbent assays ("ELISA").

Many of these methods employ an immunoglobulin molecule which is attached, or "adsorbed", to a selected matrix or "adsorption surface." For example, many ELISA techniques involve the adsorption of IgG molecules to the surface of a microtiter plate well prior to exposing the well surface to an antigen-containing sample. Similarly, antigen immunochromatography generally requires the adsorption of IgG molecules to a selected chromatography matrix. Moreover, specific immunomarking using gold-labeled antibodies has recently proved to be a powerful tool in aiding the visualization of specific antigens in a selected sample, for example, samples prepared for microscopic antigen identification. Such gold-labeled antibody complexes typically include IgG molecules absorbed to colloidal gold.

A major problem association with the development of antibody-tagged surfaces has been to achieve a surface having adsorbed antibodies arranged in a conformation which allows for proper interaction between the antibody and antigen. Immunoglobulin G molecules are composed of two separate portions, an F(c) and two F(ab) portions, arranged in a "Y" configuration wherein the two "heads" of the Y are F(ab) fragments, and the one "tail" being an F(c) fragment. In the formation of specific antigen-antibody immunocomplexes, the F(ab) ("variable") portions specifically recognize and bind the antigen, while the F(c) ("constant") portion remain unbound. Therefore, in the development of antibody-adsorbed surfaces, a preferred configuration has only the F(c) portions adsorbed to the particular surface, with the interactive F(ab) portions remaining free to bind antigen. Unfortunately, the molecular basis of IgG adsorption has previously been only poorly understood, thus leading to the preparation of mixed immunomatrices having IgG molecules adsorbed in an "head-on" (adsorbed F(ab) portion) and "side-on" configuration.

The preparation of immunocolloidal gold stain complexes with "end-on" adsorbed IgG, has proven to be particularly difficult. This is due, in part, to the need to stabilize the colloidal gold against aggregation, which includes both flocculation and coaggulation. Colloidal gold integrity appears to be a function of both pH of absorption and total concentration of protein present in the adsorption mixture (see, e.g. Geoghegan, et al. (1977), *J. Histochem. Cytochem.*, 25: 1187). Moreover, Morrisey, et al., in their study of the adsorption of IgG to latex, concluded that the molecular orientation of an adsorbed IgG is determined by the concentration of the IgG, with lower concentrations resulting in a "side-on" adsorption and higher concentrations resulting in an "end-on" adsorption (*J., Colloid Interface Sci.*, vol. 65, pp 423, 1978). Specific coaggulation and flocculation assays have been devised to test for proper gold colloidal stabilization. However, prior to the present disclosure, no one has determined the factors which account for the underlying molecular mechanisms for achieving "end-on" adsorption in the case of immunogold colloids and other immunoadsorption surfaces.

The present invention is directed to a consideration of physiochemical factors which determine selective adsorption of IgG molecules in an end-on fashion, and provides methods for achieving this preferred conformation onto positively and negatively charged adsorption surfaces. The present methods are particularly applicable to the preparation of novel immuno-gold complexes which have not heretofore been achieved.

SUMMARY OF THE INVENTION

Accordingly, the present invention relates to a method for adsorbing an IgG molecule onto a selected adsorption surface, wherein the adsorption surface has a net positive or negative charge. The method generally involves first selecting an adsorption surface having a net positive or negative charged, followed by determining an allowable IgG for the particular adsorption surface selected. For example, wherein the adsorption surface is negatively charged, an allowable IgG species comprises one having an F(c) portion with a net isoelectric point (pI) that is basic with respect to its F(ab) portion. However, in the case of a positively charged surface, an allowable IgG species is defined as one having an F(c) portion with a net pI that is acidic with respect to its F(ab) portion.

It has generally been determined that IgG populations produced by rabbits tend to have F(c) portions exhibiting a net pI that is basic with respect to its F(ab) portions. However, IgG populations from goats, sheep, horse, guinea pigs, cows, pigs, mice, rats or humans generally have F(c) portions with a net pI that is acidic with respect to their F(ab) portions. Accordingly, rabbit IgG is preferred for adsorption to negatively charged surfaces, whereas goat, sheep, horse, guinea pig, cow, pig, mouse, rat or human IgG is preferred in the case of a positively charged surface.

Thus, although the mechanism is unclear, the foregoing observation demonstrates that chemical structures having relatively acidic pI's are preferentially absorbed to positively charged surfaces and those structures having basic pI's are preferentially adsorbed to negatively charged surfaces.

Following the determination of an allowable IgG species, the method of the present invention includes fractionation of the IgG molecules of the allowable immunoglobulin species in a manner to select for a population of IgG molecules based on the pI of the individual molecules. For example, in one embodiment, referred to as the "pI range" selection criterion, a population of IgG molecules is selected wherein the population has a pI range of less than or equal to approximately 2 pI units and further wherein the net pI of the selected population is acidic, in the case of a negatively charged surface, or basic, in the case of a positively charged surface.

Numerous techniques are known in the art for the fractionation of molecules based on their isoelectric points. For example, fractionation of molecules based on their isoelectric points can be achieved through the use of ion-exchange chromatography, isoelectric focusing, isotachyphoresis, chromatofocusing, and Immobiline isoelectric focusing (LKB). However, those of skill in the art will recognize that pI fractionation may be achieved by any method which fractionates on the basis of molecular charge. All such techniques may be employed in the practice of the present invention.

Therefore, it has been determined by the present inventor that an IgG population having an overall pI range of less than or equal to approximately 2 pI units is to be preferred in order to achieve preferential adsorption of the F(c) portions of the IgG molecules. However, as noted above, where the surface is negatively charged, the net pI of the selected population should be acidic, and in the case of a positively charged surface, the net pI of the selected population should be basic. By net pI is meant the average pI of the entire selected population. For example, an IgG population having a pI range of 5–7, would have a net pI of approximately 6. Alternatively, an IgG population having a pI range of 7–9, would have a net pI of approximately 8. In the case of the former, a negatively charged surface would be preferred, and in the case of the latter, a positively charged surface would be preferred.

Therefore, wherein the selected adsorption surface is a negatively charged surface, the allowable IgG species will typically be rabbit IgG and fractionation of the IgG molecules will typically include fractionating the rabbit IgG into fractions according to their relative pI and selecting a fraction having a net acidic pI and which exhibits a pI range of less than or equal to 2. However, wherein the selected adsorption surface is a positively charged surface, the allowable IgG species will typically be selected from goat, sheep, horse, guinea pig, cow, pig, mouse, rat or human IgG, the IgG molecules being fractionated according to their relative pI and selecting a fraction having a net basic pI and which exhibits a pI range of less than or equal to 2.

In an alternative embodiment, IgG molecules of the allowable IgG species are fractionated to select for a population of IgG molecules wherein the pI values of the F(c) portions of the selected IgG molecules differ and are more basic than the pI values of the F(ab) portions of the selected IgG molecules, in the case of a negatively charged surfaces, or which differ and are more acidic than the pI values of the F(ab) portions, in the case of a positively charged surface. As with the foregoing fractionation utilized in connection with the "pI range" embodiment, the present fractionation relies on the ability to fractionate IgG molecules according to their relative pI's. However, although the fractionation is performed in a similar fashion, the criteria for selecting the proper fraction is different. That is, fractions are selected based on the identification of IgG molecules which release F(c) portions having pI's which differ from the pI's of the F(ab) portions and which are more basic in the case of a negatively charged surface, or are more acidic, in the case of a positively charged surface. Such fractions are termed "no-overlap" fractions, in that the pI's of the F(c) portions do not overlap with the observed pI's of the F(ab) portions of the selected IgG fraction. Such "no-overlap" IgG fractions are ideal for obtaining an "end-on" IgG adsorption.

Typically, selection of a "no-overlap" IgG fraction is achieved by first fractionating the IgG into fractions according to their relative pI, assaying fractions by treating an aliquot of IgG from the fraction in a manner to release free F(c) and F(ab) portions, separating the released F(c) and F(ab) portions according to their relative pI's, and selecting a fraction having IgG molecules which release F(c) portions having pI's which differ from the pI's of the released F(ab) portions.

After an adsorption surface has been selected, and allowable IgG species determined, and an appropriate IgG fraction obtained, the selected IgG population is adsorbed to the selected adsorption surface. Numerous methods are known for the adsorption of IgG molecules to surfaces. However, it has been determined that the pH at which the adsorption is carried out may be selected in a manner to achieve a selective adsorption of F(c) portions relative to F(ab) portions. Typically, a proper pH of adsorption is determined by an empirical method. For example, a portion of the selected IgG population is treated to generate free F(c) and F(ab) portions. The free F(c) and F(ab) portions are then fractionated into populations which include primarily F(c) portions and populations which include F(ab) portions. The proper pH of adsorption is then determined by adsorbing the F(ab) and F(c) portions to the surface under similar conditions at selected pH's to determine a pH at which the F(c) portions are preferentially adsorbed relative to the F(ab) portions. By preferential adsorption is meant that the F(c) portions will be more readily adsorbed at the selected pH than the F(ab) portions as, for example, determined by rate of adsorption or, alternatively, the relative amounts of F(c) portions adsorbed. In that the method is generally empirical, once a pH of adsorption has been determined for a particular IgG fraction having particular pI characteristics, that pH of adsorption is to be preferred for adsorption to that surface.

In that the methods of the present invention are believed to generate immunoadsorption matrices having a novel immuno configuration (i.e.—a "end-on" adsorption), the present invention is additionally directed to such novel immunoadsorption matrices which are made by the methods discussed herein.

BRIEF DESCRIPTION OF THE DRAWINGS

FIG. 1. Isoelectric focusing was performed in 1% IsoGel (Marine Colloids) containing 2.5% LKB Ampholines, pH 3.5–10. Samples (10 ul) containing 50 ug protein per lane, except lane 2 which contained 135 ug, were extracted into the gel for 15 minutes at 240 constant volts and then focused for 45 minutes constant power starting at 500 V (1500 V limiting). All pI values were estimated by comparison to the positions of pI markers (Pharmacia) after staining with Coomassie Blue. IgGI is the same as peak I from DE52 (WHATMAN), IgGII is the same as peak Ib from DEAE-SEPHADEX A50 following elution of the more alkaline IgG with 0.02M KPO$_4$ pH 8.0. IgG III is the same as peak III from DE52 (WHATMAN). F(ab)I was obtained from non-overlapping IgG. As is observed from the figure, its isoelectric point range (approx. 4.5–5.3) does not overlap that of the F(c) (approx. 6.2–8.15). However, the isoelectric point range of F(ab) II (approx. 4.8–8.45) overlaps the isoelectric point range of the Fc fragments (also approx. 6.2–8.15).

FIG. 3. Adsorption interaction isotherms. Colloidal gold, 18–20 nm, was prepared by the citrate method. The pH was determined by the use of a gel filled electrode and adjusted with 0.01–0.2M K$_2$CO$_3$. The minimum quantity of protein required to stabilize colloidal gold against the coagulating effects of NaCl was determined at the transition pH (the pH which marks the beginning of region 2). The isotherms were generated by the addition of the minimum quantity of protein, diluted to 1 ml with distilled water, to 5 ml of vortexing pH'd colloidal gold. After 1 minute, 1 ml of 10% NaCl was added to the vortexing protein-colloidal gold solution. After 5 minutes, the absorbance at 580 nm was determined on a Gilford spectrophotometer (1 cm light path) zeroed with a colloidal gold blank (5 ml of pH'd colloidal gold plus 2 ml of H$_2$O). The difference, a positive value, was plotted versus pH. Curves of two types were generated. A. The type I curve is divided into three regions: (1) region of protein-induced bridging or flocculation; (2) region of optimum colloid stability; and (3) region of decreasing protein colloid interaction. This region is readily distinguished only after an electrolyte (NaCl) has been added. In the absence of NaCl, the absorbance remains low and may decrease with increasing pH (dashed line). B. The type II curve is composed of two regions: 1) region of protein induced bridging or flocculation; and (2) region of optimum colloid stability.

FIG. 4. Adsorption interaction isotherms for rabbit IgG and its F(ab) and F(c) fragments. Rabbit IgG, isolated by standard procedures, was digested by papain in the presence of 0.01M DTT and separated on CM52 (Whatman). F(ab) fragments were passed over protein A-Sepharose (Pharmacia) to remove contaminating F(c) fragments. Fc fragments were bound to protein A-Sepharose to eliminate Fab and other fragments not containing both CH$_2$ and CH$_3$ domains. The purified F(c) fragments were then eluted with 0.5N acetic acid. The eluant was neutralized with tris-base and checked for purity by gel diffusion and immunoelectrophoresis using F(c) and F(ab) specific antisera. All fragments and whole IgG were dialyzed against distilled water, centrifuged to remove aggregates and diluted to 1 mg/ml before determining the minimal quantity required for stabilizsation. 4A. A, rabbit IgG DE52 PEAK I; B, rabbit F(c). 4B. A, rabbit F(ab)I; B, rabbit Fab II. See FIG. 1 for isoelectric focusing data on these proteins.

FIG. 5. Electrophoresis of stabilized colloidal gold. Protein was added to 100 ml of colloidal gold (18–20 nm particles, absorbance 0.9 at 525 nm) at the indicated pH. After 1 minute of stirring, 1 ml of 1% polyethylene glycol (20,000 MW Fisher) (PEG) was added to stabilize any colloidal gold not stabilized by the protein. After 5 minutes, the preparations were centrifuged for 1 hour at 10,500 rpm 4° C. The supernate was aspirated and the red liquid pools collected. No evidence of discolored colloid was present. The stabilized concentrate was added directly to a 3 mm well in 1% agarose (Aldrich, relative electroendosmosis −0.13)in 0.1M tricine buffer pH 8.6. The samples were electrophoresed for 100 minutes at 200 V constant. A. The minimum quatity of F(ab) I or II required to stabilize the colloidal gold at pH 6 was also added to the pH 8 and 10 colloidal gold followed after 1 minute by the addition of PEG. 1, F(ab) II-Au$_{10}$; 2, F(ab) II-Au$_8$; 3, F(ab) II-Au$_6$, 4, F(ab) I-Au$_{10}$; 5, F(ab) I-Au$_8$; 6, F(ab) I-Au$_6'$; 7, PEG-Au$_{5.5}$; B. The minimum quantity of protein required to stabilize the colloidal gold at the indicated pH was used. 1, IgG I-Au$_{10}$; 2, Fc-Au$_{10}$; 3, IgG III-Au$_{10}$; 4, IgG III-Au$_8$: 5, IgG III-Au$_6$; 6, PEG-Au$_{5.5}$.

FIG. 6. Human IgG adsorption interaction isotherms. A, F(ab) fragments; B, F(c) fragments; C, the whole IgG. Note that the F(c) fragments are unable to stabilize the colloidal gold against the coagulating effects of NaCl as the absorption pH becomes alkaline to pH8. The F(ab) end of the molecule was able to adsorb at all pH values tested. Completion between the F(c) and F(ab) ends of the IgG for the surface of the gold at pH values acidic to 7.5 was detected by the presence of protein induced flocculation (observed as an increase in absorbance). At pH values alkaline to pH 7.5, competition was reduced or absent and adsorption of the whole IgG molecule occured in the absence of protein induced flocculation.

DETAILED DESCRIPTION OF THE PREFERRED EMBODIMENTS

In its most general and overall scope, the present invention is directed to methods for achieving the adsorption of IgG molecules to positively or negatively charged surfaces. Although practice of the present invention is applicable to any positively or negatively charged surface, the invention is directed in particular to the preparation of immunocolloidal gold stains. Colloidal gold, which is generally a negatively charged surface, presents numerous additional problems in that not only must the IgG molecule be absorbed in an "end-on" configuration to achieve maximal utility, but additionally, the colloid itself must be stabilized against coaggulation and flocculation.

It has been determined that selective adsorption of the F(c) portion of the IgG molecule, relative to the F(ab) portion, is a function of various parameters, including but not limited to the net charge of the adsorption surface, the isoelectric point (pI) and pI range of the IgG population to be absorbed, the pI differential between the F(c) and F(ab) portions of the IgG, and the pH at which the IgG is adsorbed to the surface.

In general terms, it has been discovered that in the case of a net negatively charged surface, such as negatively charged colloidal gold, IgG species having an F(c) portion with a net pI that is basic with respect to its F(ab) portion is preferred. Rabbit IgG is one such species which exhibits an F(c) portion which is basic with respect to the F(ab) portion. Additional species which satisfy this criteria have not as yet been identified, however, the technique for making this determination is quite simple: an IgG population is treated with an enzyme (i.e.-papain) to release free F(ab) and F(c) portions, and the pI's of the released portions compared by, for example, isoelectric focusing. Using such techniques, an "allowable" species for the particular charged surface is identified.

Conversely, in the case of a positively charged surface, an allowable IgG species is identified as one wherein the F(ab) portions are basic with respect to the F(c) portions. It has been determined that the IgG of goat, sheep, horse, guinea pig, cow, pig, mouse, rat and human satisfy this criteria and are therefore particularly applicable in the case of absorption to positively charged surfaces.

The following table, Table I, lists a number of surfaces commonly employed as IgG adsorption matrices. However, as those of skill in the art of immunoadsorption will recognize, this list is not exhaustive and practice of the present invention is not limited to these surfaces.

TABLE I

Negatively Charged Surfaces

Nitrocellulose
Sulfonated polystyrene
Carboxylated polystyrene
Colloidal gold produced by the citrate method
Colloidal gold produced by citrate and tannic acid
Colloidal gold produced by ascorbic acid
Colloidal gold produced by phosphorus in ether
Negatively charged colloidal silver
Negatively charged nylon—carboxy groups on the surfsace (Carboxydyne, Pall)
Hydroxylated polystyrene

Positively Charged Surfaces

Colloidal AgI in the presence of excess $Ag^+$ ions
Colloidal gold whose charge has been reversed with a polyvalent cation, viz. $Th^{+3}$, $Al^{+3}$
Polysine coated surfaces, viz. polystyrene, glass
Positively charged nylon-quaternary ammonium groups on the surface (Posidyne, Pall)

The considerations which form the basis of the present invention were identified by the present inventor in connection with experimentation directed toward the development of colloidal gold labeled antibodies. Colloidal gold labeled antibodies are used in the detection of antigens on surfaces. The detection surface may be a living cell, a chemically fixed cell, or section or part of a cell. Moreover, colloidal gold immunostains may be employed in the detection of antigens present in fluids or attached to surfaces, for example, on sheets of nitrocellulose in conjunction with the so-called "western" or immunoblot procedure. The colloidal gold particles are visualized by their orange-red color, intensified with silver, or visualized in the electron microscope due to their electron density. The colloidal gold may be radioactive (e.g.—$^{195}AU$ or $^{198}AU$) or the adsorbed IgG may be radiolabeled or carry a dye or enzyme molecules. Moreover, colloidal gold has also been used in solid phase assays. Presently, colloidal gold's greatest use as in labeling specific antigenic sites on thin sections for electron microscopy.

Although the present invention is disclosed primarily in terms of a colloidal gold absorption surface, the techniques disclosed herein are equally applicable to adsorption to any charged surface. The primary distinction between adsorption to a net negatively charged surface, such as colloidal gold, and a net positively charged surface, such as positively charged nylon, is the pI characteristics of the IgG population selected for adsorption. Therefore, although the IgG fractionation procedure employed for one type of surface is basically identical to the produce employed for the alternatively charged surface, the criteria for the selection of a properly charged IgG population is basically the converse in the case of conversely charges surfaces.

A. Determination of an Allowable IgG Species

Once the charge characteristics of the selected IgG adsorption surface has been determined, it is necessary to identify an IgG species which has the proper charge characteristics for achieving end-on F(c) adsorption to that type of surface. For example, in the case of negatively charged surfaces, it is preferred to select an IgG species having an F(c) portion with a net pI that is basic with respect to its F(ab) portions. To date, only rabbit IgG has been determined to have this appropriate pI differential. However, not al IgG species have been investigated and the following technique may be employed to identify whether an IgG species is primarily suited for adsorption to a positive or negative surface.

In general, to determine the pI of the F(c) and F(ab) portions of an IgG species, it is first necessary to digest a portion of IgG with papain under conditions which will totally digest the F(c) portions of the IgG away from the F(ab) portions. Typically, a proper papain digest may be achieved by adding papain (1% w/w) to IgG at 5 mg/ml in an appropriate buffer, for example, 0.1M sodium phosphate buffer containing 0.05M sodium chloride, 0.002M EDTA and 0.01M DTT, pH 7.6. Following digestion for 15 minutes to 5 hours at 37° C., the digestion is terminated, typically by the addition of iodoacetamide to a final concentration of 0.025M, and kept dark for 15 minutes.

Following dialysis of the digestion mixture into an appropriate buffer, for example, fragments of rabbit IgG are dialyzed against 0.01M sodium acetate, pH 5.5, the papain digest is applied to a carboxymethyl cellulose column (CM 52, Whatman) previously equilibrated with 0.9M sodium acetate, pH 5.5, and washed with 0.1M sodium acetate, pH 5.5, until the conductivity and pH of the effluent are the same as the 0.01M sodium acetate, pH 5.5. A linear gradient of 0.01M to 0.9M sodium acetate buffer, pH 5.5, is applied to the column after elution of the nonbinding fraction which consists of mostly F(ab) fragments. The second peak consists of F(ab) fragments and a third peak consists of F(c) fragments. Undigested IgG and F(c) fragments are removed by passage over protein A Sepharose. F(ab) fragments are then removed from F(c) fragments by binding F(c) to protein A Sepharose and washing off unbound protein. The F(c) may be eluted with 0.5 to 1.0 normal acetic acid neutralized with tris base and dialyzed against water or 0.005M phosphate buffer (PB). For non-rabbit IgG, alternative methods for separating F(ab) and F(c) fragments are disclosed herein. Alternatively, one may desire to employ a species-specific anti-F(ab) IgG in order to remove F(ab) fragments and undigested IgG from F(c) fragments.

The relative isoelectric point (pI) of the F(c) and F(ab) portions may then be determined by isoelectric focusing (IEF), as discussed in more detail below. This step used in the context of determining an allowable IgG species, is analytical rather than preparative—its use being limited solely to assigning a pI to the F(c) and F(ab) of a particular unknown IgG species.

In the case of a positively charged adsorption surfaces, numerous allowable IgG species have been identified. For example, IgG from goat, sheep, horse, guinea pig, cow, pig, mouse, rat and human, have all been found to bear F(c) portions which are more acidic than their F(ab) portions. Therefore, where such surfaces are employed, the choice of IgG species is not as limited as in the case of a negatively charged surface. However, as additional IgG species are characterized, it is likely that additional species applicable to adsorption for negatively charged surfaces will be identified.

B. Isoelectric Point Fractionation of IgG

Perhaps the most central and fundamental aspect of the present invention is the further fractionation of the allowable IgG species to provide an IgG population having optimized charge characteristics for "end-on" adsorption. Generally speaking, charge or pI fractionation is the key to providing such a population.

In general, two non-exclusive criteria have been identified as providing a population suited to end-on adsorption. One criteria requires that the IgG species be fractionated by isoelectric point to provide a population with a net basic pI, in the case of a positively charged surface, or net acidic pI, in the case of a negatively charged surface. As noted previously, net basic or acidic pI means that the average pI of population is basic or acidic, as the case may be. This selection criteria also requires that the pI range exhibited by the population as a whole be less than or equal to 2 pI units, preferably less than 1.5 pI units.

This criteria is satisfied experimentally by, first, pI fractionation of the IgG species by one of a number of possible pI fractionation techniques. Once the IgG is so fractionated, the fractions are assayed by, for example, analytical isoelectric focusing of the fractions, to identify a fraction which satisfies the criteria.

Analytical isoelectric focusing of IgG fractions is performed typically by well known procedures. This may be accomplished most readily using 1% Isogel (Marine Colloids, Rockland, Maine) containing 2.5% ampholytes (pH 3.5–10.0, LKB, Sweden) poured on the hydrophilic side of Gelbond (Marine Colloids) to a thickness of 1 mm. Samples containing the protein are generally made free of electrolytes by dialysis and an aliquot (approx. 20 ul or less) is pipetted onto sample application wicks in separate lanes and electrophoresed into the gel at 240 volts constant for 15 minutes. The proteins are then focused by adjusting the power until 500 volts is reached. The power is maintained constant and the volts 1500 limiting allowed to adjust automatically (LKB 2197 power supply) for 45 minutes.

The gels are fixed overnight in TCA fixative (10% trichloroacetic acid, 3.45% sulfosalicylic acid dissolved in destaining solution). The fixative is removed by soaking for two days in destaining solution (500 ml of 95% ethanol, 116 ml of acetic acid diluted to 2 liters with water). The gel was stained for 15 minutes in Coumassie blue R250 (1.84 grams in 1500 ml of destaining solution) and then destained solution.

At this point the pI characteristics of the various fractions can be determined relative to known standards, and a fraction having the appropriate pI range and net pI is selected.

Alternatively, or in addition to, the pI range criteria set forth above, a further criteria referred to herein as the "no overlap" criteria may be employed. The "no overlap" criteria refers to an IgG population wherein the pI values of their F(c) portions do not "overlap" with the pI values of their F(ab) portions. To satisfy the no-overlap criteria, the non-overlapping pI's of the F(c) portions must be more basic than the pI's of the F(ab) portions, in the case of a negatively charged surface, or more acidic than the pI's of the F(ab) portions, in the case of a positively charged surface.

Experimental determination of an IgG fraction which satisfies the no-overlap criteria is performed in a manner similar to the pI range criteria. In both instances, the IgG is first fractionated according to pI. However, for no-overlap determination, aliquots from the fractions are treated with papain, as detailed above, to release free F(c) and F(ab) portions. Again, the F(ab) and F(c) portions are separated either by ion-exchange chromatography (carboxymethyl cellulose), by protein A Sepherose chromatography, by affinity chromatography, or by a combination thereof. In the case of protein A Sepharose chromatography, F(ab) fragments are removed from F(c) fragments by binding F(c) to protein A Sepharose and washing off the unbound F(ab) fragments. The F(c) may then be eluted with 0.5 to 1.0N acetic acid, neutralized with tris base and dialyzed against water on 0.005M phosphate buffer.

After separation, the F(c) and F(ab) from the various fractions are subjected to analytical pI fractionation, for example, by gel isoelectric focusing. By analysis of the fractions in this manner, one can determine a fraction, or fractions, which satisfy the no-overlap criteria. If all fraction contain overlapping F(c) and F(ab) pI's, then typically one should either choose another more sensitive pI fractionation method (for example, adopt isoelectric focusing in place of ion exchange chromatography) or alter the molarity of the starting buffer used for ion exchange chromatography.

In a more preferred embodiment, the net pI of the non-overlapping IgG from the selected fraction is acidic, in the case of a negatively charged surface, or basic, in the case of a positively charged surface.

In a still more preferred embodiment, the selected fraction satisfies both the no-overlap and pI range criteria.

C. Affinity Purification of IgG

Although not required for successful practice of the present invention, one may next desire to affinity-purify the IgG by antigen affinity chromatography prior to adsorption of the IgG to the surface. Such purification will provide an IgG population with greater specificity for a selected antigen and, additionally, tends to provide a more homogenous population in terms of pI distribution.

In general terms, to accomplish the foregoing, the particular antigen for which selectively is sought, is bound to a matrix, for example, by conjugation to a Sepharose gel. Methods for binding antigens to affinity matrices are well known in the art as, for example, detailed in *Methods in Enzymology*, Vol. 34B. One method for conjunction to Sepharose is as follows:

The gel is first washed with distilled water. A ratio of approximately 1 g of protein to 30 g of dry gel (dry weight equals approximately volume of wet packed gel divided by 1.6) is utilized. To one volume of wet gel add a volume of 2M $Na_2CO_3$, and stir slowly and chill to 5° C. Then add 2 g of cyanogen bromide per 30 g dried gel (CNBr; dissolved in $CH_3CN$ at 2 g/ml) to the chilled mixture and stir vigorously for 1–2 minutes. The mixture is then poured into a cooled sintered glass funnel and washed rapidly with 10–20 volumes of cold 0.1M $NaHCO_3$. One volume of 0.2M $NaHCO_3$ containing the dissolved protein is added and the mixture, stirred gently for 20 hours at 4° C. Then it is washed on a sintered glass funnel with 10–0.1M $NaHCO_3$ (pH above 8.0). Then, an equal volume of ethanolamine (1M in 0.2M NaHCO$_3$) is added and the mixture is stirred for about 4 hours. The mixture is then washed on a sintered glass funnel with 3M KCl in 0.1M sodium phosphate buffer, pH 7.0, and then with starting column buffer.

Next, the non-overlapping and/or pI-ranged IgG is dissolved in a buffer in which it is stable with an appropriate ionic strength to allow for the formation of an antigen-antibody complex (e.g.—0.02M phosphate buffer, 0.25M NaCl, pH 7.6). It is then passed over the matrix-bound antigen using the same buffer. After washing the column to remove unbound antibody, the specifically bound antibody is eluted with one of several solutions, for example, 0.1M acetic acid (for a low affinity antibody) followed by 0.5M acetic acid (to elute high affinity antibodies); 0.05M acetic acid, pH 2.5 0.05M glycine-HCl buffer, pH 2.5; or 0.1M acetic acid followed by 6M urea. Where 6M urea is utilized, one will need to dialyze out the urea in a step wise fashion, for example, by reducing the urea concentration in the dialysate in molar increments.

D. Adsorption of IgG Molecules to the Selected Surface

Once an IgG population has been isolated which satisfies one or both of the foregoing criteria, it is ready for adsorption to the selected surface. For surfaces other than colloidal gold, the process is quite simple. All that is required is a low ionic strength environment when the surface is contacted by the IgG-containing solution. The ionic strength should generally be lower than 0.01M, and preferably lower than 0.005M. Typically, one would want to perform the absorption in distilled H$_2$O. However, the pH of absorption may be selected so as to promote "end-on" adsorption.

For surfaces other than colloidal gold, the pH of adsorption and protein concentration is not believed to be particularly crucial. For example, some adsorption may be obtained at most any pH at which the IgG is stable. However, to obtain the more preferred end-on adsorption configuration, it is generally desirable to perform the adsorption at a pH which is more basic with respect to the most basic pI of the F(ab) of the IgG being adsorbed, in the case of a negatively charged surface, or which is more acidic than the most acidic pI of the F(ab) of the IgG being adsorbed, in the case of a positively charged surface. This allows one to take advantage of the charge differences between the F(c) and F(ab) ends of the IgG. Thus, at pH's which are basic with respect to the pI of the F(ab), the F(c) will be preferentially adsorbed to a negatively charged surface, and vice versa.

One may typically desire to use a protein concentration range of approximately 1 to 1000 ug/ml in the absorption mixture. However, a preferred protein concentration will genereally be determined as the highest concentration at which the immunoglobulin molecules are firmly adsorbed to the surface, without substantial leaching off of the protein. Radiolabeled IgG may be employed in empirical adsorption tets performed at various concentrations to determine an upper limit concentration which will provide a stable immunomatrix.

To achieve maximal "end-on" adsorption of the IgG, the determination of a proper pH is empirical. Generally, one would want to test aliquots of free F(c) and F(ab) from the IgG to be bound at various pH's to determine a pH at which the F(c) fragments are preferentially bound with respect to F(ab) fragments. This may be most conveniently accomplished using radiolabeled F(c) and F(ab) fragments, performing the adsorption of various selected pH's, and determining the relative quantity of F(c) and F(ab) adsorbed to the surface at each pH through use of the label.

For the adsorption step itself, all that is required is to bring the IgG, in low ionic strength buffer, into contact with the surface for a time period ranging from 1 minute to overnight. Again, the optimal time period for adsorption may be determined empirically. In any event, the time period is not believed to be particularly crucial.

Following adsorption, the surface is washed with any buffer in which the IgG is stable, for example, a physiological buffer. To decrease subsequent non-specific binding of antigens to the surface, one may desire to further treat the surface with solution containing BSA (bovine serum albumin), PVP (polyvinyl pyrrolidone), Twee-20, PEG (polyethylene glycol), or other agents known in the art to reduce non-specific binding to surfaces.

Adsorption to colloidal gold requires further pH and protein concentration considerations. This is due to the tendency for colloidal gold to flocculate and/or aggregate. Generally, colloidal gold is an electron dense negatively charged hydrophobic sol which binds proteins non-covalently (see, e.g., Weiser, *A Textbook of Colloid Chemistry*, Wiley & Sons, N.Y., 1949). However, colloidal gold is sensitive to electrolytes and is coaggulated by them unless stabilized by the adsorption of a protecting substance, i.e., a protein.

In 1977, Geoghegan an Ackerman (*Jrnl. Histochem. Cytochem.*, 25: 1187–1200) determine that the preparation of colloidal gold labeled protein, suitable as a marker for electron microscopy, was highly dependent on the pH of adsorption. When protein was added to colloidal gold at a pH acidic to its isoelectric point, flocculation (observed as an increase in adsorbance at 580 nm) of the colloidal gold resulted; at pH values equal to or slightly alkaline to the pI, optimal stabilization on the colloidal gold, without protein induced flocculation or NaCl induced coagulation, occurred. As the pH was adjusted to more alkaline values, proteins separated into two groups: (a) those which failed to stabilize colloidal gold against the coagulating effects on NaCl viz. albumin; and (b) those proteins which appeared to be capable of stabilizing colloidal gold thoughout the alkaline pH 7–10 range of adsorption viz. IgG. In that paper, the authors stated there were two important points to be considered with respect to the adsorption of IgG: (a) at pH 6.5 and at pH 10, the same quantity of IgG was capable of stabilizing colloidal gold against the coagulating effects of NaCl; and (b) that stabilization at pH 10 occurred even though the pH of adsorption was alkaline to the isoelectric points of all of the IgG present.

Other investigators have reported that the addition of much larger quantities of protein to colloidal gold, than determined by the coagulation test, resulted in the production of better probes. Tokuyasu (*Jrnl. Histochem. Cytochem.*, 31: 164, 1983) reported that protein A-colloidal gold (protein A-Au) complexes prepared by using 10 times the quantity of protein A recommended by Slot and Geuze (*J. Cell Biol.*, 90: 533, 1981), who used the coagulation test described by Horisberger and Rosset (*J. Histochem, Cytochem.*, 25: 295, 1977), led to a significantly higher density of labeling on sections. Horisberger and Clerc (*Histochem.*, 82: 219, 1985) reported that adsorption of protein A at high concentrations led to a progressive loss of protein A from the colloidal gold (47.6% in 84 days). By comparison, adsorption of protein A at lower concentrations resulted in a stable complex with a loss of only 0.8–1.6% by 84 days. Horisberger and Clerc recommended preparation of protein A—Au at ph 6 using the protein concentration determined by the coagulation test.

In 1984, Tinglu et al. (J. Bacteriol., 159: 668, 1984) reported that IgG-colloidal gold (IgG-Au) prepared using the quantity of IgG determined according to the coagulation test of Roth and Binder (J. Histochem. Cytochem., 26: 163, 1978) resulted in poor labeling of frozen thin sections. In their discussion, Tinglu et al. suggest that the failure to saturate colloidal gold with protein will result in non-specific labeling of cells and they reported that a ratio of 100 IgG molecules to 1 gold particle led to specific labeling.

The implication in the reports by Tokuyasu and Tinglu et al. is that the coagulation test does not predict the optimal quantity of protein required in the preparation of collodial gold-protein complexes. The data of Horisberger and Clerc suggests that the use of protein A—Au, prepared by the addition of high concentrations of protein A, will lead to variable results because the concentration of adsorbed protein A will vary continuously as a result of desorption. Unlike protein A, which is isoelectrically homogenous, serum IgG generally represents one of the most isoelectrically heterogenous proteins known and as a result, presents a more complicated problem.

With respect to the pH of adsorption of IgG to colloidal gold, therefore, two criteria should be satisfied: (1) the pH should be such that F(c) adsorption is preferred over F(ab) adsorption (discussed above), and (2) the pH should be such that the IgG-colloidal gold will not aggregate or flocculate when the IgG is added. Therefore, one would want to first determine the various allowable pH's which satisfy the second criteria, since it is the most important with respect to the integrity of the colloid. Then, one would want to determine at which of the allowable pH's the F(c) adsorption is facilitated relative to F(ab) adsorption.

To determine an allowable pH with regard to colloidal integrity, two "stickiness" tests have been developed which are believed to improve over prior tests for flocculation and aggregation. In particular, the IgG sample is dialyzed against distilled water to remove dialyzable components (i.e.—electrolytes). The antibody preparation is then centrifuged to remove aggregates and adsorbed to colloidal gold at several pH values. One minute after the addition of the IgG to the colloidal gold, one milliliter of 1% sterile, filtered polyethylene glycol (PEG; MW 20,000) is added for each 100 ml of colloidal gold.

First test for stickiness: After adsorption and five minutes after addition of the polyethylene glycol, the pH of the solution is made one pH unit more alkaline (with 0.01, 0.1 or 0.2M KOH) than the pH of adsorption (or if the pH of adsorption is 9.0 or more alkaline, the pH is adjusted to pH 10). The IgG colloidal gold complex is then centrifuged (speed and time dependent on the diameter of the collodial gold viz. 18–20 nm colloidal gold 10,500 rmp for 1 hour at 4° C.). The centrifuge tubes are removed and examined. If any discolored colloidal gold (purple, blue, black) is observed and/or if the sample is not in the form of a liquid pool at the bottom of the tube, then the sample is discarded and the adsorption step is repeated at a more alkaline pH. If the sample does not have these qualities, one continues on to the next step. It should be noted that the adjustment of the pH is also part of the regular procedure. Making the pH more alkaline enhances recovery of the product by preventing aggregation and discoloration of good preparations.

Second stickiness test: The supernate above the liquid red pool in the centrifuge tube is aspirated and the red pools combined. It has been found that IgG adsorbed at too acidic a pH may be sticky at physiological pH values. A modification of the passive gold agglutination procedure reveals this problem. A small portion of the IgG colloidal gold solution collected from the first centrifugation step is adjusted to an absorbency of 0.6 at 525 nm with 0.01M sodium phosphate buffer, 0.9% NaCl, 1% polyethylene glycol pH 7.3 (PBS-P). A standard V-well microtiter plate is used. Twenty five microliters of PBS-P is added to each well. Next, 25 $\mu$l of IgG-colloidal gold is added to each well. The microtiter plate is covered with sealing tape and vibrated on a (e.g.—a Cooke micromixer) for 75 seconds and allowed to incubate at room temperature for 20 minutes. The plate is vibrated a second time and then centrifuged at 20°–22° C. for 10 minutes at 3,000 rpm. The plastic cover is removed and the plate tilted at a 45° angle. For a good preparation, the dark reddish dot at the tip of each well begins to form a red tail and after 30–60 minutes, the material completely resuspends itself without leaving aggregated colloidal gold behind. If any portion of the material is left unsuspended after this time or if any of the IgG-colloidal gold remains aggregated, then the pH of adsorption must be made more alkaline.

Once a satisfactory pH has been determined, larger quantities of colloidal gold are stabilized with the IgG, polyethylene glycol added and the pH adjusted as described in the "First test for stickiness". The supernates are carefully aspirated and the dark red liquid pools of IgG-colloidal gold are combined.

Trace amounts of any unbound IgG are removed by chromatography on Bio-Gel A column equilibrated with 0.01M sodium phosphate buffer plus 0.15M NaCl plus 0.02 mg polyethylene glucol per milliliter pH 7.3. To date, all proteins adsorbed to colloidal gold and passed through these columns have done so without sticking to the beads (<1% estimated). Small aggregates are generally deposited at the top of the gel. The particular Bio Gel A is chosen such that any unbound protein is separated from the protein-colloidal gold. The particular Bio Gel A which permits this and which results in the sharpest and narrowest protein colloidal gold peak is selected.

The IgG-colloidal gold is collected, adjusted to the desired absorbency and may then be sterile filtered into a sterile container.

EXAMPLE 1

Adsorption of Rabbit IgG to Colloidal Gold

I. Purification and pI Fractionation of Rabbit IgG

Rabbit antiserum (200 ml) was first precipitated twice with an equal volume of saturated ammonium sulfate, pH 6.8, at 22°. The precipitate was redissolved after each precipitation in 1 volume of 0.1M sodium phosphate, pH 7.6 (PB). The precipitated protein was then dialyzed against 3 changes of 4 liters of 0.01M PB (24 hours each change).

90 grams of DEAE (DE-52, Whatman) was added very gently to 0.2 molar PB buffer and the pH adjusted to 7.6 with 0.2 molar monobasic or dibasic phosphate buffered phosphate until the pH remained constant at 7.6. The DE-52 was stirred gently overnight. In the morning it was allowed to settle and then excess buffer poured off. Starting buffer (0.01 molar PB, pH 7.6) was added and the DE-52 poured into 2.5×35 centimeters glass column. The column was run at 4° C.

The starting PB was passed through the column until the conductivity and pH of the eluent equaled that of the starting PB. The dialyzed protein was centrifuged at 20,000 rpm for 30 minutes and was then passed through the column. The unbound IgG was designated peak I, and the tubes containing protein as determined by absorbency at 280 nm were pooled. Peak I was found to consist primarily of proteins with a pI of greater than 5.5 (see IgGI in FIG. 1).

When the absorbency of the column was less than 0.05 at 280 nm, the starting buffer was replaced by 20% buffer (eight volumes of starting buffer mixed with 2 volumes of 0.02 molar sodium phosphate buffer plus 0.1 molar sodium chloride, pH 7.6). A second peak, peak II, eluted when the 20% buffer was applied. Peak II was found to consist of protein with isoelectric points less than pH 7 (see IgGIII, FIG. 1).

Due to the fact that the colloidal gold was negatively charged, and peak I contained proteins of relatively higher pH's than peak II, the pooled peak I fractions were subjected to further pI fractionation in order to isolate an appropriate fraction for adsorption.

Using this procedure, rabbit IgG was resolved into multiple fractions by rechromatography on DEAE Sephadex A50 (approximately 50 grams). The A50 was equilibated overnight with 0.3M potassium phosphate ($KPO_4$) buffer, pH 8.0. The A50 was then washed extensively with a more dilute $KPO_4$ (0.02M $KPO_4$, pH 8.0), until the conductivity and pH of the eluent were equal to the starting buffer. The column was run at 4° C. Trial runs were performed starting with 0.02M KPO4, pH 8.0, to choose a proper starting buffer. Decreasing the molarity of the buffer used to equilibrate the column increases the quantity of IgG bound to the A50. At 0.005M $KPO_4$ pH 8.0, most of the IgG is bound. The protein is then eluted in small steps 0.005M, 0.01M, 0.015M, 0.02M, etc. $KPO_4$ pH8. Analytical isoelectric focusing may then be used to determine which molarity yields the fractions of interest, for example, proteins which exhibit an isoelectric point range of 5.7 to 7.4.

After an appropriate starting buffer was determined (in this case the starting buffer used was 0.02M KPO4, pH 8.0), a small quantity (less than 200 mg) of Peak I IgG was passed over the column. The unbound fractions were collected and pooled.

A linear gradient increasing to 0.3M KPO4, pH 8.0, was then applied to the column. Generally, one peak is eluted by the gradient (see IgG II from FIG. 1). Multiple peaks, when not well resolved, should be rechromatographed to eliminate contamination of the larger peaks by the smaller ones. A sample of each peak was set aside for analytical isoelectrophoresis.

In order to analyze the column fractions for compliance with the non-overlap criterion, a papain digest was first performed as follows: Papain (1% w/w) was added to IgG at 5 mg/ml in 0.1M sodium phosphate buffer containing 0.05M sodium chloride, 0.002M tetrasodium EDTA and 0.01M DTT, pH 7.6, and allowed to digest at 37° C. for 4 to 5 hours. Digestion was terminated by the addition of iodoacetamide to a final concentration of 0.025M, and kept dark for 15 minutes. The digestion mixture was then dialyzed against four liters of 0.1M sodium phosphate buffer plus 0.9% NaCl, pH 7.2. Next, the mixture was dialyzed against 3 changes of 0.01M sodium acetate buffer, pH 5.5, 24 hours each change.

Next the papain digest was applied to a carboxymethyl cellulose column (CM 52, Whatmann) previously equilibrated with 0.9M sodium acetate, pH 5.5, and washed with 0.01M sodium acetate, pH 5.5, until the conductivity and pH of the effluent are the same as the 0.01M sodium acetate, pH 5.5. A linear gradient of 0.01M to 0.9M sodium acetate buffer, pH 5.5, was applied to the column after elution of the nonbinding fraction which consists of mostly F(ab) fragments. The second peak consisted of F(ab) fragments and a third peak consists of F(c) fragments.

All fragments were dialyzed against 0.1M sodium phosphate buffer containing 0.9% sodium chloride, pH 7.3 (3 changes—2 liters each). Undigested IgG and F(c) fragments were removed by passage over protein A Sepharose equilibrated with the same buffer. F(ab) fragments were then removed from F(c) fragments by binding F(c) to protein A Sepharose and washing off unbound protein. The F(c) were eluted with 0.5 to 1.0 normal acetic acid neutralized with tris base and dialyzed against water or 0.005M PB. F(ab) fragments and undigested IgG starting material were also dialyzed against water or 0.005M PB.

The isoelectric point range of the F(c) and F(ab) fractions and isoelectric point standards were then determined by isoelectric focusing in 1% Isogel (Marine Colloids, Rockland, Maine) containing 2.5% ampholytes (pH 3.5-10.0, LKB, Sweden) poured on the hydrophillic side of Gelbond (Marine Colloids) to a thickness of 1 mm. Samples containing the protein (approx. 20 ul or less) were pipetted onto sample application wicks in separate lanes and electrophoresed into the gel at 240 volts constant and the volts 1500 limiting allowed to adjust automatically (LKB 2197 power supply) for 45 minutes.

The gels were fixed overnight in TCA fixative (10% trichloroacetic acid, 3.45% sulfosalicylic acid dissolved in destaining solution). The fixative was removed by soaking for two days in destaining solution (500 ml of 95% ethanol, 116 ml of acetic acid diluted to 2 liters with water). The gel was stained for 15 minutes in Coumassie blue R250 (1.84 grams in 1500 ml of destaining solution) and then destained in destaining solution.

The mobility of the F(c) fragments was then compared to the mobility of the F(ab) fragments. If there was no overlap, and the F(ab) fragments were more acidic than the F(c) fragments, then the IgG was considered to be a non-overlapping IgG (compare F(ab)I and F(c), FIG. 1). If there were overlap between the F(c) and the F(ab) fragments, then the molarity of the starting buffer on the DEAE Sephadex A-50 was increased. This results in a larger peak Ia (unbound fraction) and a smaller second peak.

As noted previously, subfractionation of the IgG by DEAE chromatography may be replaced at any point by preparative isoelectric focusing in agarose in a granulated gel (LKB Ultradex) or in Agarose-Sephadex, by chromatofocusing or by Immobiline isoelectrofocusing (LKB). Additionally, any other separation technique which fractionates on the basis of pI may be employed. Moreover, total IgG may be fractionated directly by one of these procedures without the initial fractionation on DEAE cellulose. However, it is believed that the initial DEAE fractionation ultimately provides an overall cleaner pI fractionation.

II. Iodination of Rabbit IgG

In order to provide a labeled IgG for use in conjunction with adsorption experiments, rabbit IgG (DEAE peak II fraction) was trace labeled with 125 Iodine by a modification of the Bio Rad solid phase lactoperoxidase-glucose oxidase procedure (Bio Rad, Tech. Bulletin 1071) which is normally used to label protein to a high specific activity. The procedure was modified to label rabbit IgG with a low specific activity to reduce damage to the molecule. This was achieved by increasing the quantity of protein and by decreasing the quantity of Na 125 I added. Briefly, 5 mg IgG (centrifuged in a Beckman TL 100 centrifuge in a TL 100.2 rotor at 100,000 rpm for 10 minutes and concentration then determined) in 0.5 ml of 0.2M sodium phosphate buffer, pH 7.1, was added to Enzymobeads (Bio Rad, Richmond, DA; single reaction size) rehydrated in 0.5 ml of PB. 100u Ci Na 125-1 (New England Nuclear, Boston, MA; low pH, medium concentration) was added followed by 250ul of fresh 1% B-D-glucose. The mixture was rocked gently at 22° C. for 1 hour and aspirated gently through a 0.2 micron filter into a syringe to remove the Enzymobeads, thus stopping the iodination. The mixture was then dialyzed extensively against normal saline to remove free iodine and then against distilled deionized water to remove electrolytes. The rabbit IgG was found to have specific activity of $2.46 \times 10^{-3}$ uCi/ug IgG.

Figure 2:
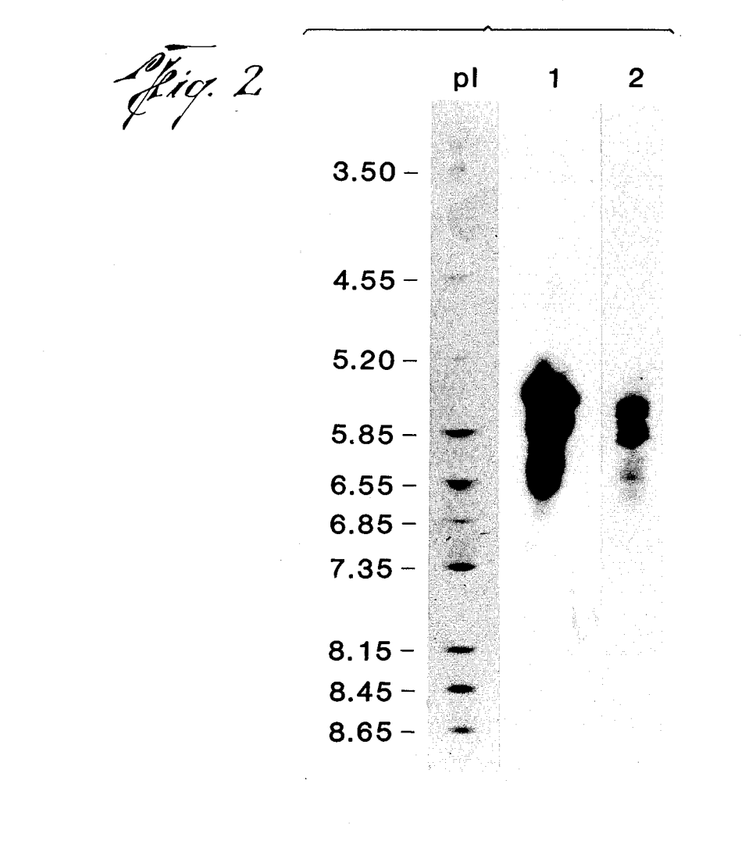
FIG. 2. Isoelectric focusing of radiolabeled (lane 1) and unlabeled (lane 2) rabbit IgG. Lane 1 20 ul sample (23.2 ug protein), lane 27 ul sample (52 ug protein).

To demonstrate that the ion exchange fractionation procedure provided an IgG population which satisfied the pI range criteria, and further, to demonstrate that the iodination procedure did not result in a major pI shift, the pI range of labeled and unlabeled, fractionated rabbit IgG was determined. In FIG. 2, the positions of the Coomassie blue stained pI markers and non-radiolabeled IgG are compared to the positions of the 125-I-rabbit IgG. The position of the radioactivity in lane 1 is nearly identical to the less sensitive Coomassie stained area in lane 2. Faint lines in lane 2 (not detectable in the photograph) match the position of the acidic end of the image in lane 1. Further, the isoelectric point range of most of the protein is between pI markers 5.20 and 6.85, which represents a relatively uniform and acidic fraction of the IgG population present in rabbit serum. In particular, it is shown that the pI range of the peak II DEAE fraction is approximately 1.5, with the net pI being approximately 6.0.

III. Preparation of Colloidal Gold

Colloidal gold was prepared by the "citrate method" by reducing chloroauric acid ($HAuCl_4$, ICN Pharmaaceuticals) with trisodium citrate (see, e.g., Frens (1972), *Kulloid Z.v.Z. Polymere*, 250: 736). Using a porcelain spatula, chloroauric acid (0.1 g) was added to 1 liter of triple distilled deionized water and brought to a boil. This solution was stirred vigorously on a magnetic stirrer as 25 ml of a fresh solution of 1% aqueous trisodium citrate was rapidly poured into the boiling solution. As the solution boils it turns dark blue and with continued heating for several minutes longer the color changes to a clear orange-red representing the reaction endpoint. Large batches of colloidal gold were made in this manner and stored for further use. Colloidal gold particles produced were essentially uniform in size averaging 18-20 nm in diameter but may be produced in a variety of sizes up to 147 nm by decreasing the quantity of trisodium citrate added (Frens (1973), *Nat. Phys. Sci,* 241: 20). Although the citrate method was employed for this study, numerous additional methods are known in the art for the preparation of colloidal gold, as exemplified by tannic acid-sodium citrate, *European J Cell Biology* 38: 87, 1985; Thiocyanate, *Histochemistry* 83: 409, 1985; White phosphorus, *Immunocytochemistry: Applications in Pathology and Biology* (Ed Polak and Van Noorden). Other references include the sodium ascorbate method (Horisberger (1979), *Biol. Cellulaire*, 36: 253) and other general methodology (Weiser, *Textbook of Colloid Chemistry*, 1949, Wiley and Sons; Weiser, *Inorganic Colloid Chemistry*, Vol. 1 and 2, Wiley and Sons). Any such method may be employed in the practice of the present invention.

Colloidal gold prepared using the citrate method has a pH between 5 and 6. The pH of the colloidal gold may be adjusted after cooling by addition of small quantities of either 0.2M $K_2CO_3$ to make it more basic or it can be made more acidic by the addition of 1M $H_3PO_4$ or 1M acetic acid depending on the molecules to be adsorbed.

The pH was determined using a gel filled electrode (Marson, Phoenix, AZ). All preparations were pH-adjusted and used for adsorption within 1-2 hours. The pH remained constant ±0.03 pH units throughout all adsorption steps. The colloidal gold used in these experiments had an absorbency of 0.889 at 525 nm (the spectrophotometer was zeroed with $H_2O$).

IV. pH of Adsorption

Figure 3:
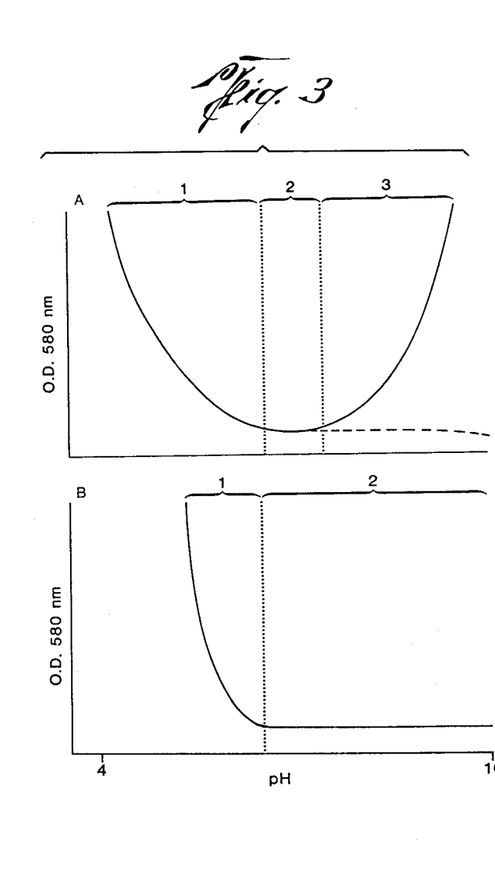

In addition to pH selection based on preferential F(c) adsorption, which may be determined empirically as discussed previously, in the case of colloid gold it is generally desirable to select a pH of adsorption at which the colloid will not aggregate. One method which has been found by the present inventor to identify a non-aggregating pH is by plotting what is referred to herein as adsorption interaction isotherm curves (FIG. 3).

Differences in the adsorption of rabbit IgG and its fragments are reflected in the shapes of such curves which are composed of 2 to 3 regions relating to the interaction of protein and/or NaCl with colloidal gold over a defined pH range. For production of a non-flocculated colloidal gold-protein complex, the conditions present in region 2 are desirable. However, it is the transition from region 1 to region 2 and the transition from region 2 into region 3 which provide information about the protein-colloidal gold interactions. Unlike polyethylene glycol (PEG), a non-ionic polymer which adsorbs at all pH values without causing flocculation, all proteins tested to date cause flocculation of colloidal gold at some acidic pH value. Protein induced flocculation, region 1, is probably due to increased protonation of amino acids at acidic pH values in conjunction with a decrease in the number of negative charges. This is supported by data clearly linking the isoelectric point of the protein, the pH of the colloidal gold and the absence or presence of flocculation. Competition between different positively charged sites on the protein molecule for the surface of the negatively charged gold would result in the bridging of two or more particles by a single protein molecule.

The transition from region 1 to region 2 (the most acidic pH at which the protein may be added to colloidal gold without flocculation) marks the end of this vigorous competition and the beginning of the adsorption of individual protein molecules to one gold particle only. This suggests that some parts of the molecule are successful in adsorbing while other parts remain unbound and exposed to the aqueous compartment. The result would be a particular orientation. As a result of orientation, the ability of an adsorbed protein to bind or react with a dissolved molecule would be determined by the accessibility of that site (conformational changes in the adsorbed species must be considered ultimately). Within region 2, the pH of adsorption might be varied as a means of influencing molecular orientation and conformation. In addition, changes in the pH of adsorption of protein to colloidal gold influence the quantity of protein which may be bound by the gold.

The transition from region 2 to region 3 is not detected spectrophotometrically until NaCl is added. This observation together with a gradual increase in absorbance as the pH becomes more alkaline suggests that the interaction between the protein and the gold is decreasing. The decreased interaction is probably due to deprotonization of the protein and a subsequent increase in repulsive negative charges. Mutual repulsion would become increasingly more important as more groups were deprotonated and as the proteins' negative charges increased. For some proteins, a complete failure to adsorb would ensue resulting in the type I curve. For other proteins, molecular orientation might provide equal stabilization for the colloidal gold within the pH limitations tested (pH 4–10). This would result in the type II curve.

Figure 4A:
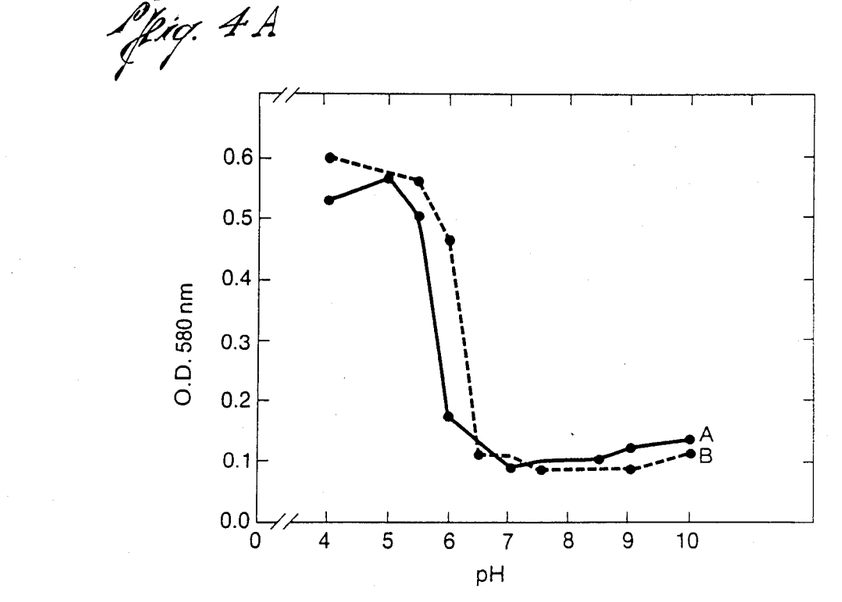
Figure 4B:
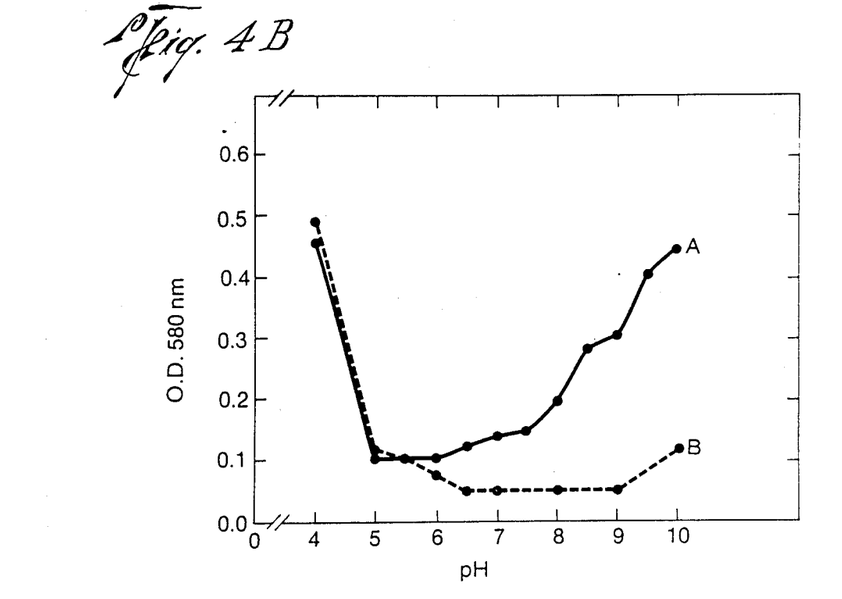

Adsorption interaction isotherms for rabbit IgG and three of its fragments prepared from the same pool of IgG were constructed (FIG. 4). Although these curves do not conform exactly to the idealized schematic (FIG. 3), major trends are readily observed. The most acidic protein, F(ab) I, yielded an adsorption interaction isotherm distinct from that of the more alkaline and isoelectrically heterogeneous proteins. F(ab) I exhibited the most acidic transition pH and the narrowest region 2. Region 3 is characterized by a gradually increasing absorbance suggesting a gradual decrease in the interaction of the F(ab) I with the colloidal gold. The remaining three proteins had more alkaline transition pH's and a wide region 2. At pH values alkaline to 9, the IgG and F(c) exhibited a slight increase in absorbance while that of F(ab) II was somewhat more pronounced.

Figure 5:
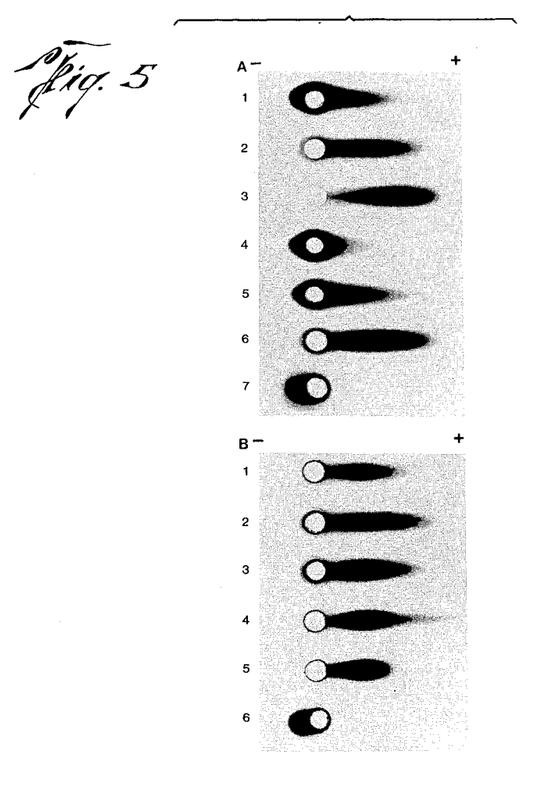

If the changes in absorbance in the adsorption interaction isotherms reflect changes in the adsorption of protein, then the effects of these changes should be detectable. To substantiate this, F(ab) I and II were adsorbed at pH 6, 8, and 10 and then were compared to one another by electrophoresis. The agarose used produces an electroendosmotic (EEO) effect, a flow of water towards the cathode, which causes uncharged PEG-Au to move in that direction. The proteins, however, move in the direction of the anode at pH 8.6 against the flow of water. The combination of electrophoretic mobility and EEO used effectively in immunoelectrophoresis, separates PEG-Au from F(ab)-Au. The electrophoretic results demonstrate that changes in the electrophoretic mobility correspond to changes in the adsorption interaction isotherms (FIG. 5). F(ab) I, adsorbed at pH 6 (F(ab) $I_6$), moved towards the anode without leaving a cathodic component behind. F(ab) $I_8$ and $I_{10}$, however, separated into two components, a fraction which moved towards the cathode and a fraction which moved towards the anode.

Figure 1:
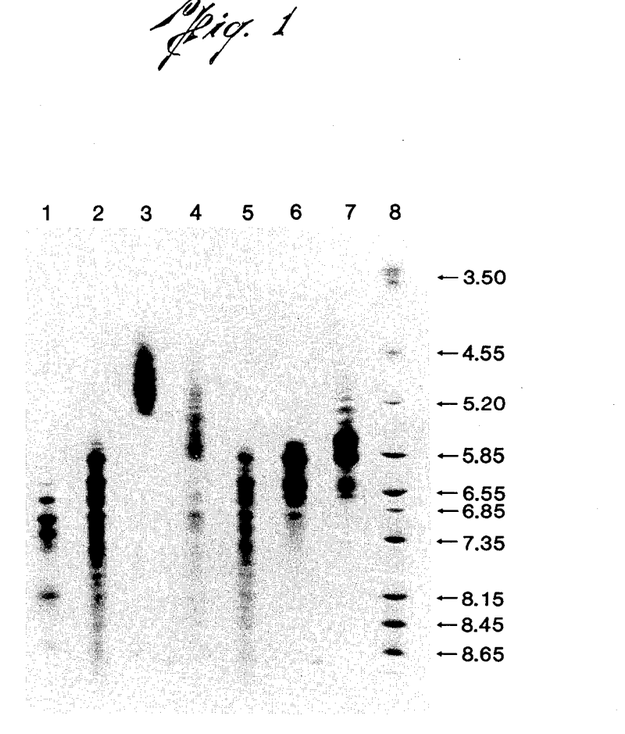

F(ab) I was found to be composed of acidic fragments with a relatively narrow pH range (4.3–5.4) (FIG. 1). The electrophoretic data suggest that a significant quantity of F(ab) I adsorbed at pH 6, while fewer molecules adsorbed at pH 8 and 10. Coagulation of F(ab) $I_8$ and $I_{10}$ was prevented by the addition of PEG and the resemblance of the mobility of a portion of each of these two samples to preparations of PEG-Au is probably due to the adsorption of PEG in place of non-adsorbing acidic F(ab) I fragments. By comparison, F(ab) $II_6$, and $II_8$ moved in the direction of the anode. F(ab) $II_{10}$ appeared, like F(ab)$I_8$ and $I_{10}$ to be composed of two components. F(ab) II is composed of acidic and alkaline fragments with a broad pH range (4.8–8.9) (FIG. 1). The mobility of the anodic components for F(ab) I and II exhibited a decrease in the rate of movement as the pH of adsorption becomes more alkaline. This method may also be used to determine a pH at which the F(ab) fails to adsorb or adsorbs poorly in a one minute time interval. For example, an IgG composed of two F(ab)$_1$ fragments and an F(c) fragment might preferably be adsorbed at a pH between 8 and 10, where the presence of PEG-Au is observed (FIG. 5). Ideally the fraction should be adsorbed at 0.5 pH intervals beginning at the transition pH or the whole IgG and then electrophoresed to determine a proper pH of adsorption, for example, where PEG-Au formation occurs.

Figure 6:
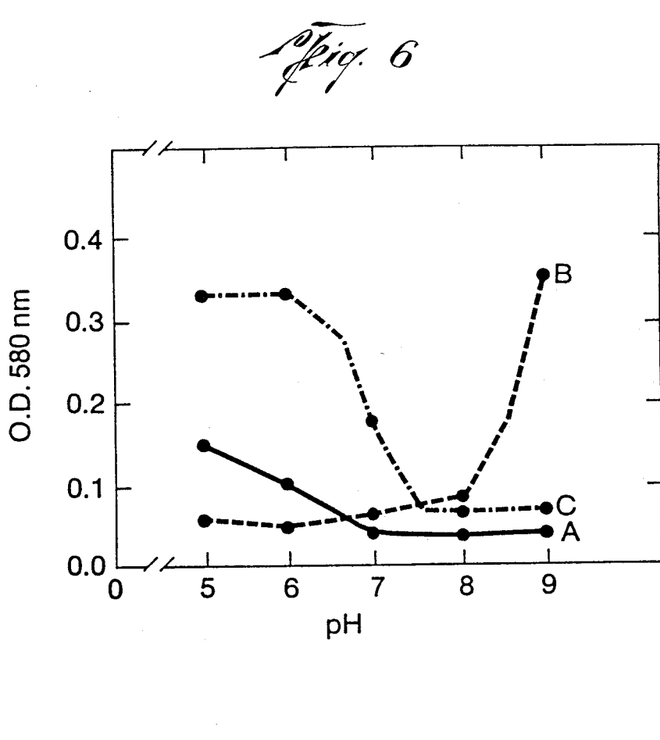

The adsorption interaction isotherms in FIG. 6 demonstrate the effect of an acidic F(c) fragment and a relatively more alkaline F(ab) on preferrential adsorption of one end of an IgG molecule over the other end. Adsorption of this human IgG, at pH 9, is expected to occur by way of the F(ab) end of the molecule (A) and the F(c) end (B) would not adsorb and stabilize colloidal gold against the effects of NaCl at this pH. By comparison, rabbit F(c) fragments adsorb to and stabilize colloidal gold against the effects of NaCl at the same pH.

V. Absorption of IgG to Colloidal Gold

Non-overlapping rabbit to IgG was dissolved in distilled water, centrifuged to remove aggregates and the concentration adjusted to less than 1 mg IgG/ml. The pH of the colloidal gold (O.D. 525 nm 0.9±0.02) was adjusted to 1 pH unit more alkaline than the midpoint pH of the isoelectric point range of the IgG (0.01, 0.2 or 0.2N $K_2CO_3$ was used to make the pH more alkaline and dilute pohosphoric or acetic acid was used to make the pH more acidic). The purpose was to select the most acidic pH which permited the addition of the protein without resulting in protein induced flocculation. The minimum quantity of IgG required to prevent coagulation of the colloidal gold by the addition of NaCl was then determined. A series of IgG solutions was prepared in distilled water (final volume 1 ml). The IgG concentrations were adjusted from 10 ug/ml to 150 ug/ml at 10 ug increments. These values were based on the use of 18–20 nm colloidal gold particles. A decrease in particle diameter will result in an increase in surface area and hence more protein will be required (the reverse is true for larger particles).

One millimeter (ml) of the aqueous IgG was added to 5 ml of colloidal gold in a glass test tube, and the solution was stirred in a vortex by a vortex mixer. Vortexing was continued for 10–15 seconds or until complete mixing of the protein and the colloidal gold solution was achieved. After 1 minute, 1 ml of 10% NaCl was added as the solution was vortexed. This process was repeated for each protein sample. A sample blank was prepared by the addition of 2 milliliters of distilled water to 5 ml of vortexing colloidal gold. The spectrophotometer was zeroed at 580 nm using this blank. Five minutes after the addition of NaCl to the protein-colloidal gold sample, the absorbance was determined and recorded. This was performed for each concentration of IgG used. The absorbance was plotted on the y axis versus protein concentration on the x axis. The minimum quantity of protein required to prevent NaCl induced coagulation is the point where the curve first appears asymptotic with the x axis. This concentration was used to determine region 2 and the transition pH.

A series of colloidal gold solutions ranging in pH from 4 to 10 at 0.5 pH unit intervals were prepared by the addition of dilute phosphoric acid, acetic acid or (0.01, 0.1, 0.2N) $K_2CO_3$. The minimum quantity of protein, in 1 ml of water, required to prevent coagulation was added to 5 ml of each colloidal gold sample (pH 4–10) vortexed, NaCl added after 1 minute and absorbance determined as described above. The absorbance, y axis, was plotted versus the pH of absorption, x axis, and regions 1 and 2 (and sometimes 3) determined. Generally, a pH value within region 2 was selected for a trial absorption.

The pH of 100 ml of colloidal gold, in a clean flask, was adjusted to the desired pH. A gel-filled electrode was used in all pH adjustments. These have a very low electrolyte flow rate and do not cause coagulation of the colloidal gold. In addition, gel filled electrodes are not plugged up by colloidal gold. Twenty times the minimum quantity of protein required to stabilize 5 ml of colloidal gold was added (less than 1 mg/ml concentration) with stirring. After 1 minute, 1 ml of 1% polyethylene glycol (MW 20,000) was added and the solution stirred for five minutes. The pH of the solution was then adjusted to a pH value 1 pH unit more alkaline to the pH of adsorption. The preparation was then centrifuged at 10,500 rpm for 1 hour (first test for stickiness).

The minimum quantity of IgG required to prevent coagulation of colloidal gold may be replaced by a larger quantity of IgG provided that the resulting IgG-colloidal gold preparation does not release significant quantities of IgG, viz. greater than 3% back into the solution (desorption). This is tested by the use of 125-I labeled IgG. Radiolabeling is performed such that low specific activity is achieved. The radiolabeled IgG is then diluted with 9 parts cold IgG and after dialysis against distilled water, the quantity desired is added to colloidal gold and adsorbed. The sample is subjected to both tests for stickiness and then passed over a Bio Gel A column to remove unbound or free IgG. The colloidal gold peak is sterile filtered and stored for 1–4 weeks. After this time period, the sample is centrifuged, for example, at 40,000 rpm for 20 minutes in a Beckman TL 100 using a TLS-55 rotor. The supernate is collected and counted. Trichloracetic acid (TCA) is added (final concentration 5%) to the supernate and the TCA precipitable cpm determined. This value should represent less than 3% of the total cpm minus the percent that was unbound in the same sample at time storage began.

EXAMPLE 2

IgG Adsorption to Sulfonated Polystyrene

Non-overlapping rabbit IgG from animals immunized with, for example, horseradish peroxidase (HRP), is fractionated on DE-52 as described above and the peak II fractions, pI 5.2–6.5, are collected. The pooled fractions are then affinity purified on HRP-Sepharose 4B, eluted with 0.5N acetic acid, neutralized, and dialyzed against distilled water. Isoelectric focusing of a papain digest of the affinity purified IgG should reveal the presence of F(ab) fragments with maximal alkaline mobility and net pI equal to about 5.3. After centrifugation to remove aggregates, the concentration of the undigested, affinity-purified IgG is adjusted to about 60 ug IgG/ml. Dilute potassium carbonate is added to adjust the pH to 7.6 and the IgG is pipetted in 267 ul amounts into each well of a 96 well flat bottom microliter plate composed of sulfonated polystyrene. The plates are then incubated for 3 hours at 22° C., and overnight at 4° C. Unbound protein is aspirated off and the wells rinsed three times with 0.01M sodium phosphate buffer, pH 7.6. The walls are then incubated with hemoglobin and IgG-free 1% bovine serum albumin in 0.01M sodium phosphate buffer, pH 7.6, non-specific containing 0.9% NaCl (PBS) for 1 hour to block free sites. The plates are then rinsed three times with PBS.

EXAMPLE 3

Adsorption to Poly-L-Lysine-Coated Polystyrene

A non-overlapping human IgG is prepared from a patient with, for example, syphilis. The most acidic F(ab) fragment from a papain digest of the IgG should demonstrate a pI of, for example, about 8.3. After centrifugation to remove aggregates the concentation of the IgG, dissolved in water, is adjusted to about 60 ug/ml. The pH is adjusted to 7.0 using dilute acetic acid or dilute $K_2CO_3$. The solution in 267 ul amounts is added to each well of a poly-L-lysine-coated polystyrene 96-well flat-bottom microliter plates. The plates are incubated for three hours at 22° C. and overnight at 4° C. Unbound protein is aspirated and the wells rinsed three times with 0.01M sodium phosphate buffer pH 7.0. The wells are then incubated with hemoglobin and IgG free 1% BSA in 0.01M sodium phosphate buffer pH 7.2 containing 0.97NaCl (PBS) for 1 hour to block any non-specific sites. The plates are then rinsed three times in PBS.

EXAMPLE 4

Adsorption of Mouse Monoclonal IgG to Quaternary Ammonium Modified Nylon

A non-overlapping mouse monoclonal antibody $IgG_1$ from ascites fluid is selected. Its F(ab) fragments generally have a maximal acidic pI of 8.1. It is dissolved in water and the pH adjusted to 7.0 with dilute tris acetate buffer, pH 7.0 (or with $K_2CO_3$, pH 7.0). If not soluble in water, the IgG is dissolved in a phosphate buffer in which it is soluble, and then dialyzed against 0.005M tris acetate, pH 7.0. After centrifugation to remove aggregates, the concentration is adjusted to 60 ug/ml.

The protein is then added to nylon membrane filters which have been prewet in 0.05M tris acetate, pH 7.0. The nylon is, for example, modified to contain quaternary ammonium groups on its surface. The IgG is incubated with the membrane for 1 hour followed by three rinses with 0.01M sodium phosphate buffer+0.9% NaCl (PBS) pH 7.0 before incubation with IgG-free 1% bovine serum albnumin in PBS for 1 hour. The membrane is then rinsed three times with PBS.

EXAMPLE 5

Purification of Non-Rabbit Mammalian IgG

Most non-rabbit mammalian IgG is readily separated from serum proteins by precipitation with saturated ammonium sulphate, as described for the rabbit, followed by chromatography on DEAE gels.

In a general procedure, mammalian IgG may be chromatographed on DEAE in 0.01M sodium phosphate buffer. The initial pH generally determines how much of the IgG binds and how much elutes. Generally, the pH of the buffer is 6.3–8.0 and is held constant. After elution of the unbound IgG more IgG is eluted by stepwise increases in the molarity of the buffer; for example 0.2, 0.3, 0.4, 0.5M. The gradient may also be continued by the addition of NaCl viz. 0.05M, 0.01M, 0.2M etc. to the column buffer.

Murine ascites fluid containing monoclonal antibody is precipitated twice by the addition of saturated ammonium sulfate to a final concentration of 45% and washed two times with 40% saturated ammonium sulfate. The precipitate is redissolved each time with 0.01M sodium phosphate buffer containing 0.9% sodium chloride, pH 7.6. The IgG is dialyzed against 0.005M tris phosphate buffer, pH 8.6, and is applied to a DEAE cellulose column (DE 52, Whatman) equilibrated with the same buffer. All or nearly all of the sample will bind. Elution is achieved in a stepwise manner by adding a series of buffers prepared as follows—The pH of the starting buffer is adjusted to pH 8.2, 8.0, 7.8, etc., by the addition of a 3:1 mixture of 0.005M tris phosphate, pH 8.6, and 0.5M tris phosphate, pH 5.1. IgG fractions are collected. Alternatively, or in addition, it may be necessary to use preparative isoelectric focusing to obtain a fine separation. Preparative IEF, for example, using Immobiline, permits the use of very restricted pH ranges for separation.

Ascites fluids are generally contaminated with non-monoclonal immunoglobulins requiring the use of affinity chromatography before selection for non-overlapping IgG. Moreover, IgG2B and IgG3 tend to precipitate at low ionic strength, especially near their pI, whereas IgG1 is usually soluble. The more alkaline murine IgG, especially of the IgG1 subclass, are preferred. This permits adsorption at low ionic strength and at a pH acidic to the pI of the F(ab) and at a pH removed from that of the IgG. Competition between the F(c) and R(ab) end of the IgG for an adsorptive matrix favors the F(c) end of the IgG as the difference in the pI values of the F(c) and F(ab) increase.

Mouse IgG is often contaminated with transferrin. This may be removed on protein A-Sepharose (0.1M phosphate buffer pH 8.0). The transferrin is washed away and the IgG eluted with 0.1M citrate phosphate buffer pH 5.0–2.2. Transferrin may also be removed with anti-mouse transferrin-Sepharose or by hydroxyapatite chromatography. Human IgG may be purified using the general procedure. Starting pH is usually pH 8.0.

Fractions may be tested by papain digestion, as described, for example, for non-rabbit IgG, and purified by, for example, preparative isoelectric focusing, as described above for rabbit IgG. Affinity chromatography may also be utilized at any point in the purification. Monoclonal antibodies may be purified on DEAE, affinity chromatography, protein-A-Sepharose and/or an hydroxyapatite chromatography (HA) to remove small quantities of non-IgG proteins. IgG equilibrated with 0.001M phosphate buffer pH 6.8 is added to an HA column equilibrated with the same buffer. The protein are eluted from HA by increasing the molarity of the phosphate buffer either stepwise or in a linear gradient from 0.001M to 1.0M pH 6.8.

EXAMPLE 6

F(ab), F(c) Preparation and Purification in Non-Rabbit Mammals

In most mammals, for example, goat, sheep, mouse, human, horse, guinea pig, rat, and the cow, the F(ab) fragment is generally less acidic than the F(c) fragment and DEAE chromatography may be used for their separation. For example, a papain digest of goat IgG is dialyzed against 0.01M sodium phosphate buffer pH 7.5 (starting buffer) and applied to DEAE (DE52 Whatman may be used) column, previously equilibrated with 1.0M sodium phosphate pH 7.5, and washed with starting buffer until the effluent and starting buffer have the same conductivities and pH. Unbound protein is collected and a linear gradient of 0.01M to 1.0M sodium phosphate buffer pH 7.5 is applied to the column. The first two peaks contain F(ab) fragments. The third peak is the F(c). Papain digests of isoelectrically homogenous IgG, viz., isoelectric point range 5.5–6.0, 7.5–8.0 may only yield one F(ab) peak.

Protein A-Sepharose equilibrated with 0.1M phosphate buffer pH 7.2–9.0 depending on species, for example, rabbit pH 7.2; mouse pH 8.0; guinea pig pH 9.0 may be used to remove undigested IgG or contaminating F(c) fragments from the F(ab) except where the F(c) is not bound due to subclass and species differences where F(c) protein A binding does not occur efficiently enough viz. human IgG$_3$; goat and sheep IgG, some subclasses of rat and mouse IgG. Species specific anti-F(c)-Sepharose may be used to remove all F(c) fragments. F(ab) contamination of F(c) may be eliminated by passage of the F(c) fragments over species specific anti-F(ab) Sepharose. Moreover, determining the isoelectric point range of the fragments is the same as for the rabbit fragments.

what is claimed is:

1. A method for preparing an adsorption surface by adsorbing thereon selected IgG molecules, the method comprising the steps of:
    (a) selecting an adsorption surface having a net positive or negative charge;
    (b) choosing an IgG species having an F(c) portion with a net pI that is basic with respect to its F(ab) portion in the case of a negatively charged surface, or an F(c) portion with a net pI that is acidic with respect to its F(ab) portion in the case of a positively charged surface;
    (c) fractionating IgG moieties of the chosen IgG species to select for a population of IgG molecules having a pI range of less than or equal to approximately 2 pI units and further wherein the net pI of the selected population is acidic, in the case of negatively charged surface, or basic, in the case of a positively charged surface; and
    (d) adsorbing the selected IgG population to the selected adsorption surface.

2. The method of claim 1 wherein the selected adsorption surface is a negatively charged surface, the chosen IgG species is rabbit IgG, and step (c) comprises:
    (a) fractionating the rabbit IgG into fractions according to their relative pI; and
    (b) selecting a fraction having a net acidic pI and which exhibits a pI range of less than or equal to 2.

3. The method of claim 2 wherein the selected negatively charged adsorption surface is negatively charged colloidal gold.

4. The method of claim 1 wherein the selected negatively charged adsorption surface is negatively charged nitrocellulose, negatively charged polystyrene, negatively charged colloidal gold, negatively charged colloidal silver, or negatively charged nylon.

5. The method of claim 1 wherein the selected adsorption surface is a positively charged surface, the chosen IgG species is goat, sheep, horse, guinea pig, cow, pig, mouse, rat or human IgG, and step (c) comprises:
   (a) fractionating the IgG into fractions according to their relative pI; and
   (b) selecting a fraction having a net basic pI and which exhibits a pI range of less than or equal to 2.

6. The method of claim 5 wherein the selected positively charged adsorption surface is positively charged colloidal gold, positively charged polystyrene, or positively charged nylon.

7. The method of claim 1 further comprising a step of selecting a pH of adsorption at which adsorption of the F(c) portion of the selected IgG population will be facilitated relative to adsorption of the F(ab) portion and wherein the step (d) is performed at the selected pH.

8. The method of claim 7 wherein selecting a pH of adsorption comprises the steps of:
   (a) enzymatically digesting an aliquot of the selected IgG population to generate free F(c) and F(ab) portions;
   (b) adsorbing the free F(c) and F(ab) portions to the surface at various pH's to determine a pH at which the F(c) portions are preferentially adsorbed relative to the F(ab) portions; and
   (c) selecting the pH determined in step (b) for performing the adsorption of the selected IgG population.

9. A method for preparing an adsorption surface by adsorbing thereon selected IgG molecules, the method comprising the steps of:
   (a) selecting an adsorption surface having a net positive or negative charge;
   (b) choosing an IgG species having an F(c) portion with a net pI that is basic with respect to its F(ab) portion in the case of a negatively charged surface, or an F(c) portion with a net pI that is acidic with respect to its F(ab) portion in the case of a positively charged surface;
   (c) fractionating IgG molecules of the chosen IgG species to select for a population of IgG molecules wherein the pI values of the F(c) portions of the selected IgG molecules differ and are more basic than the pI values of the F(ab) portions of the selected IgG molecules, in the case of a negatively charged surface, or which differ and are more acidic than the pI values of the F(ab) portions, in the case of a positively charged surface; and
   (d) adsorbing the selected IgG population to the selected adsorption surface.

10. The method of claim 9 wherein the net pI of the selected population is acidic, in the case of negatively charged surface, or basic, in the case of a positively charged surface.

11. The method of claim 9 wherein the selected adsorption surface is negatively charged, the chosen IgG species is rabbit IgG, and step (c) comprises:
   (a) fractionating the IgG into fractions according to their relative pI;
   (b) assaying fractions by an aliquot of IgG from the fraction in a manner to generate free F(c) and F(ab) portions;
   (c) separating the F(c) and F(ab) portions according to their relative pI's; and
   (d) selecting a fraction having IgG molecules with F(c) portions having pI's more basic than the pIs of the F(ab) portion.

12. The method of claim 11 where in the IgG molecules of the selected fraction exhibit a net acidic pI.

13. The method of claim 11 wherein the adsorption surface is negatively charged colloidal gold.

14. The method of claim 11 wherein the selected negatively charged adsorption surface is negatively charged nitrocellulose, negatively charged polystyrene, negatively charged colloidal gold, negatively charged colloidal silver, or negatively charged nylon.

15. The method of claim 9 wherein the selected adsorption surface is positively charged, the chosen IgG species is goat, sheep, horse, guinea pig, cow, pig, mouse, rat or human, and step (c) comprises:
   (a) fractionating the IgG fractions according to their relative pI's;
   (b) assaying fractions by an aliquot of IgG from the fraction in a manner to generate free F(c) and F(ab) portions;
   (c) separating the free F(c) and F(ab) portions according to their relative pI's; and
   (d) selecting a fraction having IgG molecules with F(c) portions having pI's more acidic than the pI's of the F(ab) portions F(ab).

16. The method of claim 15 wheren the IgG molecules of the selected fraction have a net basic pI.

17. The method of claim 15 wherein the selected positively charged adsorption surface is positively charged colloidal gold, positively charged polystyrene, or positively charged nylon.

18. The method of claim 9 further comprising a step of selecting a pH of adsorption at which adsorption of the F(c) portion of the selected IgG population will be facilitated relative to adsorption of the F(ab) portion and wherein step (d) is performed at the selected pH.

19. A method for adsorbing an immunoglobulin molecule onto a selected adsorption surface comprising the steps of:
   (a) selecting an adsorption surface having a net positive or negative charge;
   (b) choosing an IgG species having an F(c) portion with a net pI that is alkaline with respect to its F(ab) portion in the case of a negatively charged surface, or an F(c) portion that is acidic with respect to its F(ab) portion in the case of a positively charged surface;
   (c) selecting a pH of adsorption at which adsorption of the F(c) portion to the surface will be facilitated relative to adsorption of the F(ab) portion; and
   (d) adsorbing the IgG to the selected adsorption surface at the selected pH.

20. The method of claim 19 wherein selecting a pH of adsorption comprises the steps of:
   (a) enzymatically digesting an aliquot of the selected IgG species to generate free F(c) and F(ab) portions;
   (b) adsorbing the free F(c) and F(ab) portions to the surface at various pH's to determine a pH at which the F(c) portions are preferentially adsorbed relative to the F(ab) portions; and (c) selecting the pH detemined in step (b) for performing the adsorption of the selected IgG population.

21. The method of claim 19 wherein the selected adsorption surface is a negatively charged surface and the chosen IgG species is rabbit IgG.

22. The method of claim 20 wherein the adsorption surface is colloidal gold.

23. The method of claim 20 wherein the selected negatively charged adsorption surface is negatively charged nitrocellulose, negatively charged polystyrene, negatively charged colloidal gold, negatively charged colloidal silver, or negatively charged nylon.

24. The method of claim 19 wherein the selected adsorption surface is a postively charged surface and the chosen IgG species is goat, sheep, horse, guinea pig, cow, pig, rat, mluse or human IgG.

25. The method of claim 24 wherein the positively charged adsorption surface is positively charged colloidal gold, positively charged polystyrene, or positively charged nylon.

* * * * *

UNITED STATES PATENT AND TRADEMARK OFFICE
CERTIFICATE OF CORRECTION

PATENT NO. : 4,880,751
DATED : November 14, 1989
INVENTOR(S) : William D. Geoghegan It is certified that error appears in the above—identified patent and that said Letters Patent is hereby corrected as shown below:

On the title page, in item [75] Inventor, delete "Georghegan" and insert --Geoghegan--.

In claim 1(c), column 24, line 51, delete "moieties" and insert --molecules--.

In claim 5, column 25, line 11, delete "a positively charged surface" and insert --positively charged--.

In claim 5, column 25, line 12, delete "IgG".

Signed and Sealed this

Seventeenth Day of September, 1991

Attest:

HARRY F. MANBECK, JR.

Attesting Officer

Commissioner of Patents and Trademarks